United States Patent [19]

Lorenzen et al.

[11] Patent Number: 5,253,331
[45] Date of Patent: Oct. 12, 1993

[54] EXPERT SYSTEM FOR STATISTICAL DESIGN OF EXPERIMENTS

[75] Inventors: Thomas J. Lorenzen, Rochester Hills; William S. Spangler; William T. Corpus, both of Warren; Lynn T. Truss, Royal Oak, all of Mich.

[73] Assignee: General Motors Corporation, Detroit, Mich.

[21] Appl. No.: 725,123

[22] Filed: Jul. 3, 1991

[51] Int. Cl.[5] ............................................. G06F 15/18
[52] U.S. Cl. ..................................... 395/50; 364/554; 395/919
[58] Field of Search .................... 364/550, 554; 395/1, 395/919

[56] References Cited

U.S. PATENT DOCUMENTS 4,658,362  4/1987  Bhatt ................................. 364/472
5,079,690  1/1992  Li ...................................... 364/148

OTHER PUBLICATIONS

Johnson et al., Statistics and Experimental Design, John Wiley & Sons, 1977, 593–604, 794–795, 825–828, 942–950.

Minor, M., "Expert Systems, Graphics Capabilities Add Flexibility to Statistical Software", PC Week vol. 5(6), Feb. 1988, 93–95.

Schwartz, S., "Reviews–Statistical Analysis Software", MACWORLD, May 1990, 375–379.

Chen, F. T., "A Personal Computer Based Expert System Framework for the Design of Experiments", Computers in Ind. Engineering vol. 21 (1–4), 1991, 197–200.

"An Expert System for Experimental Design in Off-Line Quality Control" Newton S. Lee, Madhav S. Phadke, and Rajiv Keny.

T. J. Lorenzen & L. T. Truss, "Dexpert ... Design of Experiments Using Expert Reasoning Tools," Aug. 1989, pp. 1–16, Research Publication, General Motors Research Laboratories, Warren, Mich. 48090.

Primary Examiner—Michael R. Fleming
Assistant Examiner—Robert W. Downs
Attorney, Agent, or Firm—A. Frank Duke

[57] ABSTRACT

An expert system for the design and analysis of experiments includes a descriptive mathematical model of the experiment under consideration. From this mathematical model, expected mean squares are computed, tests are determined, and the power of the tests computed. This supplies the information needed to compare different designs and choose the best possible design. A layout sheet is then generated to aid in the collection of data. Once the data has been collected and entered, the system analyzes and interprets the results.

4 Claims, 7 Drawing Sheets

Experiment Information

| Factor | Abb. | Type | Quant/Qual | Levels | Nested/Sliding Factors |
|--------|------|------|------------|--------|------------------------|
| A | A | Fixed | Quant | 2 | |
| B | B | Fixed | Qual | 2 | |
| C | C | Random | Qual | 2 | A B |

Number of Repetitions
2

◁ ▷

[ New Factor ] [ Edit Factor ] [ Rename Factor ] [ Delete Factors ] [ Run Order Restrictions ] [ Change Factor Levels ] [ Done ]

FIG - 2

Response Factor Information

Factor: C
Qual/Quant: QUANTITATIVE
Factor Abbreviation: C
Unit of Measure: Unknown
Lower Limit: 1
Upper Limit: 10

[Cancel] [Change to Qualitative] [New Factor] [Done]

FIG - 7

Factor Information

Factor: B
Unit of Measure: Unknown
Factor Abbreviation: B
Number of Levels: 2
Nested/Sliding Factors: Unknown
Fixed/Random: FIXED
Qual/Quant: QUALITATIVE

[Cancel] [New Factor] [Done]

| Design Name | | Experiment Mode | | | Number of Repetitions | Experiment Size |
|---|---|---|---|---|---|---|
| Design 1 | | Full Factorial | | | 2 | 16 |

| Term | Test Type | Tested By | Delta | Detectable Size |
|---|---|---|---|---|
| A | DIRECT | C | 1.55 | MEDIUM |
| B | DIRECT | C | 1.55 | MEDIUM |
| AB | DIRECT | C | 2.2 | MEDIUM |
| C (AB) | DIRECT | error | 2.66 | MEDIUM |
| error | NONE | NONE | UNDEFINED | — |

[Suggestions] [Redesign] [All / Control] [Notepad]

◁ [Verbal Interpretation] [Show Additional Information] [Print Design Information] [Approve Design]
▷

Results Information

| Design Name | Response Variable | Number of Repetitions | Experiment Size |
|---|---|---|---|
| Design 1 | Y | 2 | 32 |

| Term | Test Type | Tested By | MS | F Test | P Value |
|---|---|---|---|---|---|
| E | DIRECT | I | 0.848 | 0.492 | 0.70662 |
| I (E) | DIRECT | error | 1.722 | 1.632 | 0.21480 |
| F | INSIGNIF. ONLY | IF | 0.045 | 0.013 | 0.91543 |
| restrI (F) | NONE | NONE | ---- | ---- | ---- |
| EF | DIRECT | IF | 1.886 | 0.536 | 0.68238 |
| IF (E) | DIRECT | error | 3.521 | 3.337 | 0.03620* |
| error | NONE | NONE | 1.055 | ---- | ---- |

[Assumptions] [Pooling] [Previous Pooling] [Additional Analyses] [Show Additional Information]

◁
▷ [Continue Search] [Re-Analyze] [Graphical Displays] [Print Results] [Notepad]

FIG - 5

Fractionation Information

Terms of Interest

| | |
|---|---|
| Main Effects | All |
| 2-factor | A*B B*C |
| 3-factor | None |
| 4-factor | None |
| 5-factor | None |

Terms not Confounded with Terms of Interest

None
A*C A*D A*E B*D B*E C*D C*E D*E
None
None
None

[Directions] [Retrieve Previous Info] [Edit Terms of Interest] [Edit Terms not Confounded] [Cancel] [Done]

FIG - 6

Results Information

| Design Name | | Response Variable | | Number of Repetitions | | Experiment Size |
|---|---|---|---|---|---|---|
| Design 4 | | Y | | NIL | | 23 |

| Term | Test Type | Parameter | Std Error | T Value | P Value |
|---|---|---|---|---|---|
| intercept | DIRECT | 11.950 | 16.643 | 0.718 | 0.48546 |
| A | DIRECT | -3.726 | 4.095 | -0.910 | 0.37952 |
| AA | DIRECT | 0.285 | 0.368 | 0.776 | 0.45163 |
| B | DIRECT | -4.913 | 4.095 | -1.200 | 0.25168 |
| BB | DIRECT | 0.240 | 0.368 | 0.654 | 0.52461 |
| AB | DIRECT | 1.407 | 0.592 | 2.378 | 0.03343* |
| C | DIRECT | 6.810 | 4.095 | 1.663 | 0.12026 |
| CC | DIRECT | 0.151 | 0.368 | 0.410 | 0.68883 |
| AC | DIRECT | -1.281 | 0.592 | -2.165 | 0.04959* |
| BC | DIRECT | -0.906 | 0.592 | -1.531 | 0.14974 |
| error | NONE | ----- | ----- | ----- | ----- |

◁ [Assumptions] [Pooling] [Previous Pooling] [Additional Analyses] [Show Additional Information]
▷ [Continue Search] [Re-Analyze] [Graphical Displays] [Print Results] [Notepad]

FIG - 8

EXPERT SYSTEM FOR STATISTICAL DESIGN OF EXPERIMENTS

FIELD OF THE INVENTION

This invention relates generally to expert systems and more particularly to an expert system that interacts with users to statistically design experiments.

BACKGROUND OF THE INVENTION

Since its introduction by R. A. Fisher, the design of experiments has played an important role in agricultural and scientific studies. Genichi Taguchi has recently renewed the interest of product and process engineers in design of experiments techniques.

Design of experiments is the first step in a process to evaluate how factors influence response variables. An experiment design may be defined as a data collection sheet which specifies how the values of the input factors of the experiment are to be set for each trial of the experiment. This data collection sheet is an essential ingredient for accurate, efficient experimentation. To produce an efficient experiment design the statistician makes use of a statistical analysis software package, such as for example, SAS available from SAS Institute. They may then go further and evaluate this design by hand, a long and tedious process even with the use of a computer.

Currently expert systems are available for designing experiments but are limited to selection from a limited class of designs. See for example, "An expert system for experimental design in off-line quality control" by Lee, Phadke, and Keny in Expert Systems, November, 1989, Vol. 6, No. 4 page 238. Prior to this invention there were no other means available for automatically generating and analyzing the power of balanced experimental designs. Rather than forcing the user to accept one of a predetermined set of experiment designs, the expert system of the present invention generates a design meeting the user's requirements and evaluates that design.

SUMMARY OF THE INVENTION

In accordance with the present invention an expert system is provided which can interface with a client to generate and analyze balanced designs using a linear models approach, expert reasoning abilities, and existing software packages. The expert system of the present invention emulates the role of a consulting statistician, interacting with the client to gather information needed to generate the descriptive mathematical model and physical layout of the experiment.

The role of the expert system of the present invention is to bridge the gap between the user, an engineer who is inexperienced in statistical techniques, and the SAS package. It interacts with the user to identify the goal of the experiment, the input factors involved, how they relate to one another, whether there are nested factors (i.e. factors whose levels depend on the levels of other factors). Once the necessary information has been collected from the user the expert system writes appropriate SAS code to generate an experiment design. The results returned from these procedures will constitute enough information to produce an experimental design.

However, before producing a data collection sheet, the expert system evaluates and refines the design through the use of a mathematical model. The expert system advises the user about any problems with the design, presents alternatives for improving the design, and identifies advantages and disadvantages of each alternative. Once the user is satisfied with the tradeoffs associated with a particular experiment design, the expert system generates the data collection sheet of that design. When this data collection sheet has been filled in with actual experimental results, it requires only a simple call to a few SAS procedures to determine which particular input factors or interactions affect the response variable(s).

BRIEF DESCRIPTION OF THE DRAWINGS

The above and other advantages of the invention will become more apparent from the following description taken in conjunction with the accompanying drawings wherein like references refer to like parts and wherein:

FIG. 2 and 3 are forms for gathering user inputs.

FIG. 4 is a form for displaying design information.

FIG. 5 is a form for displaying analysis information.

FIG. 6 and 7 are forms for gathering user inputs.

FIG. 8 is a form for displaying analysis information.

DETAILED DESCRIPTION

Figure 1:
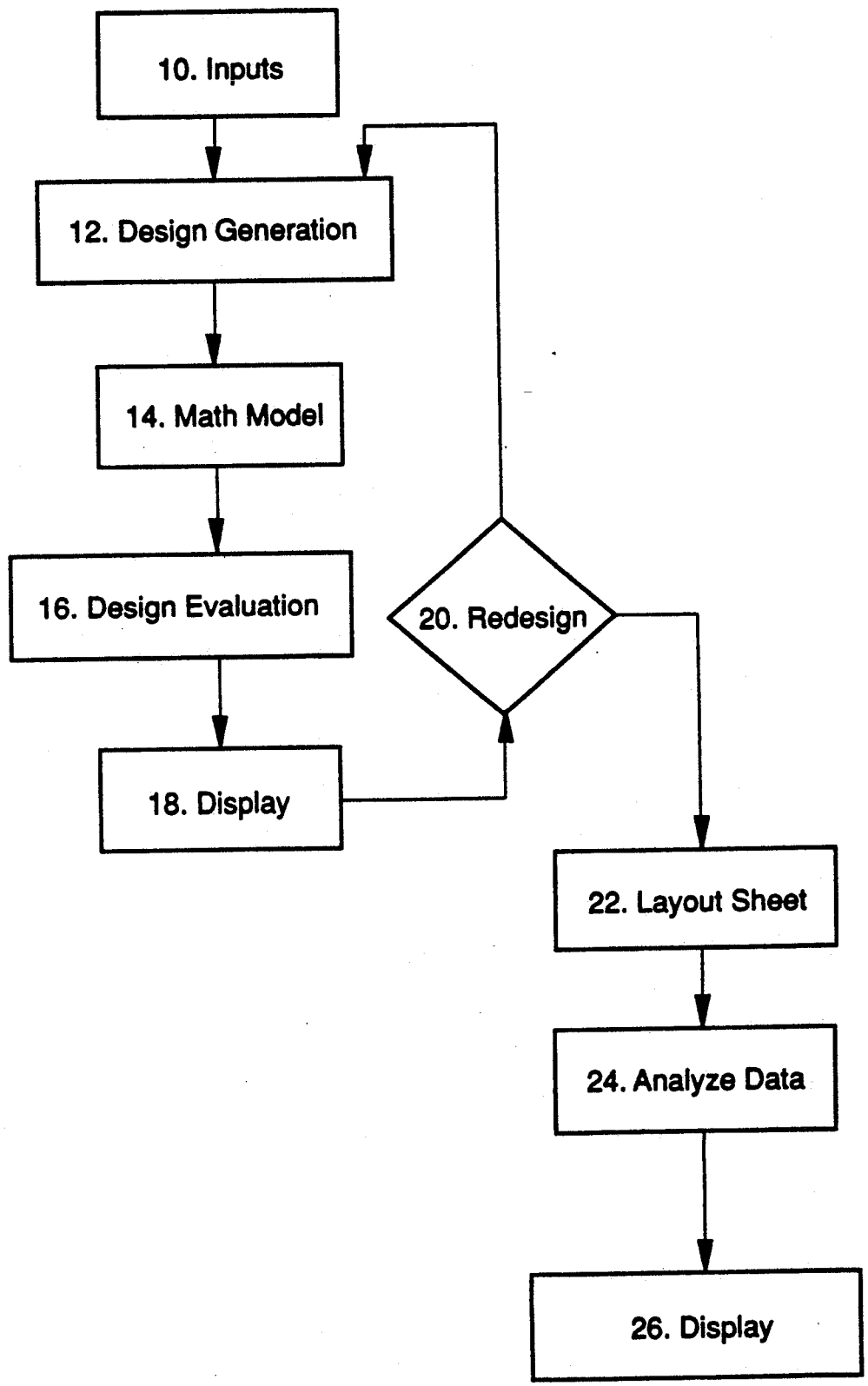
FIG. 1 is a generalize flow chart of the present invention.

Referring now to the drawings and initially to FIG. 1, the expert system of the present invention requires five basic pieces of information. In the preferred embodiment the expert system is primarily programmed in KEE, a Lisp based knowledge engineering environment, running on a Sun 4 Workstation. The inputs required, as indicated by block 10, are:

1. The goal of the experiment, which must be one of the following:
   a. Complicated Influence
   b. Screening
   c. Robust Design
   d. Model Response
2. The Response Variables, which are the names of the numerical measurements which will be taken after each trial of the experiment—there must be at least one.
3. The Factors, which are the names of the variables in the experiment—those things which the experimenter changes from one trial to the next.
4. Factor Properties, i.e. information which is required about each factor's statistical properties and (potentially) about possible interactions between different factors. The information required will differ somewhat depending on the type of experiment.
5. Run Order Restrictions wherein the user restricts the order in which the experiment trials may be run in order to make the experiment more practical. This restriction is represented as an ordered list of factors, hardest to change factors listed first.

Some additional information may be required depending on the type of experiment. This will become apparent hereinafter.

The data as input by step 10 provides the necessary information to generate the design as indicated in block 12. The method for generating the design will depend on the goal of the experiment.

The design generation block 12 provides the necessary information to produce a math model representation of the experiment as indicated at Block 14. This model consists of the addition of a series of terms which represent the effect of:

1. Factors
2. Factor Interactions

3. Restrictions on Run Order
4. Experimental Error

The inputs of step 10, the design generated in step 12 and the math model generated in step 14 provide the basis for evaluating the experiment design as indicated in block 16. For each term in the math model a detectable difference (delta) value is calculated. This information helps the user determine whether or not an experiment is worthwhile before it is run.

The calculations in block 16 are displayed to the user in a forms interface as indicated in block 18. A suitable forms software package is available from IntelliCorp. The system also provides an English summary of the design information upon request.

Having viewed the design, a user may wish to make modifications to the original input information of block 10 in order to produce a design which better suits their requirements. Upon request, the expert system suggests potential ways to modify the input information to achieve desired design objectives as indicated in block 20.

Once a design is approved a layout sheet is produced as indicated in block 22 which serves as a detailed plan for how to run the experiment. For each trial of the experiment the layout sheet lists the combination of factor levels (settings) and leaves space for recording the results in terms of response variable values. The layout sheet is produced using the SAS package.

After the user runs the experiment and collects results, the expert system analyzes the experiment data as indicated in block 24. The type of analysis used will depend on the goal of the experiment.

The calculations in block 24 are presented to the user in a forms interface as indicated at block 26.

COMPLICATED INFLUENCE

Inputs (block 10)

When the complicated influence goal is selected by the user, inputs are gathered from the user through a series of interactive forms which are shown in FIGS. 2 and 3. The factor information is stored in the KEE frames structure. A class unit is set up, called FACTORS which contains slots for storing critical information about the factors of the experiment. Each factor is represented as an individual unit which is a child of the FACTORS class. Each child of the FACTORS class inherits slots for storing the user's input. The following slots store the critical information for each of the user's factors in complicated influence:

1. Abbreviation—a short string used to represent the factors effect in the math model representation.
2. Number of Levels—The number of distinct values that each factor can take on.
3. Type—Must be either fixed or random. A factor is fixed if a specific level for that factor is selected and inferences are to be made about that specific level. A factor is random if the level is representative of an entire population and the inference is to be made to the population, not the specific level.
4. Quantitative-or-Qualitative—A factor is quantitative if it has meaningful numbers associated with its levels. Otherwise it is qualitative.
5. Nesting—A random factor may be nested in one or more other factors. This implies that the levels of this factor will depend on the levels of another factor or factors.
6. Sliding—A fixed factor may be sliding in one or more other factors. This implies that the levels of this factor will depend on the levels of another factor or factors.

In addition to information on individual factors the user also enters the number of repetitions (i.e. number of times each combination of factor levels will be run in the experiment) and any run order restrictions (i.e. an inability or disinclination to change the levels of a factor frequently from one experiment trial to the next).

Generate Design (block 12)

Complicated influence experiments begin by generating a full factorial design. Every possible combination of factor levels is represented in this design.

Generate Math Model (block 14)

A full Mathematical model that includes all possible factor interactions, is generated to correspond with this design. This is generated using the following algorithm.

1. Start with the first factor abbreviation, for example A, and attach the lower case subscript i yielding $A[i]$.
2. (Non-nested case) Take the next factor abbreviation, for example B, and attach the next subscript (alphabetically) and form all interactions with the previous terms. For example, add $B[j]$ yielding the terms $A[i]$, $B[j]$, and $AB[ij]$. Continue in this fashion for all non-nested factors.
2. (Nested-case) For nested factors attach the next subscript (alphabetically) but also attach the subscripts associated with all nesting factors inside the parentheses. For example, if C were nested within A, use the notation $C[k(i)]$. If C were nested in A and B use the notation $C[k(i,j)]$. Again form the interaction with all other terms separately combining subscripts outside parentheses and inside parentheses. Do not include any terms that have the same index inside and outside the parentheses. For example, if B were nested in A, and D within C, the complete set of terms would be $A[i]$, $B[j(i)]$, $C[k]$, $AC[ik]$, $BC[jk(i)]$, $D[l(k)]$, $AD[il(k)]$, and $BD[jl(ik)]$. $AB[ij(i)]$ is not included because i appears inside and outside the parentheses.
3. Restrictions on run order randomization are included in the mathematical model as follows. If the factor abbreviated as A is restricted this indicates that complete randomization is replaced by the process of selecting a level of A and running all factor levels combinations involving this level before selecting another level of A. This is denoted with the addition of a random term "restr" having one level and nested in A. Restriction error terms do not interact with any other term in the model. If it is desired to restrict both A and B (equally) then this would cause a restriction to fall on the AB interaction. If A is harder to change than B, we can add to restrictions—one on A and another on the AB interaction.
4. All effects in the experiment which are not fixed at a given level and not related to the input factors are represented by the error term which is nested in every other factor. Thus the error term for a three factor experiment would be $error[l(ijk)]$.

The mathematical model for the experiment then becomes the sum of all the individual terms. For example, an experiment with two factors A and B having no nesting or restrictions would have the following mathematical model:

$$A[i] + B[j] + AB[ij] + error[k(ij)]$$

Design Evaluation (block 16)

The mathematical model generated (block 14) and the inputs (block 10) and the design (block 12) are the basis for evaluating the properties of the design. These properties include:

1. Degrees of Freedom for each Term (df)
2. The type of test available on each Term
3. The terms testing each Term
4. The test degrees of freedom for each Term
5. The detectability of each term (delta)
6. A classification for the detectability for each term
7. The Expected Mean Squares for each term (EMS)
8. The required experiment size (number of runs)

Since all of these designs are balanced, the df are computed using well-known formulae, e.g. Peng, K. C. (1967), The Design and Analysis of Scientific Experiments. The formulae depend on the number of levels for each factor and the nesting pattern. The total experiment size is simply the product of the levels of each factor times the number of repetitions. The remainder of the calculations are based on the EMS.

The calculation of the EMS is based on an algorithm published by Lorenzen, T. J. (1977), Derivation of Expected Mean Squares of Ftests in Statistical Experimental Design, Research Publication GMR-2442: Mathematics Department, General Motors Research Laboratories, Warren Mich. 48090-9055 incorporated herein by reference. This algorithm is equivalent to the standard algorithm given by Bennett and Franklin (1954), Statistical Analysis in Chemistry and the Chemical Industries. The EMS's are represented as a square matrix with dimension equal to the number of terms in the mathematical model. Each row corresponds to a given term in the mathematical model. The matrix is filled with zeros and ones. The matrix is set up so that all values below the diagonal are zero. A one in a column indicates the corresponding column term is in the EMS for that row term. If df=0 for a term, all elements in the corresponding row are 0. Separate vectors store the coefficients associated with each column and whether the row terms are fixed or random. The square matrix, coefficient vector, an term type vector completely determines the EMS for each term. For a detailed example, see page 9 of Research Publication GMR 7111 dated Jul. 31, 1990 by Lorenzen and Truss available from the General Motors Research Laboratories, Warren Mich. 48090-9055, which is incorporated herein in its entirety.

The next step is to determine the type of test available on each term. The test is a ratio. The numerator is the row of the matrix which represent the EMS of the term we are trying to test and the denominator refers to the row of the matrix which represents the EMS of the term which provides the test.

DIRECT tests are looked for first. A term Y directly tests term X if the EMS for Y equals the EMS for X with the X component (diagonal element) set to zero.

If there is not a direct test available then the expert system looks for an APPROXIMATE test. An APPROXIMATE test is a linear combination of terms whose EMS form a DIRECT test. With a square matrix, add and subtract linear combinations of rows to equal the row corresponding to x with the diagonal element set to zero. The approximate df associated with this test is the harmonic mean of the terms involved in the linear combination. The search algorithm to find this linear combination is as follows:

1. Start with the row in the matrix corresponding to the term of interest. Call this row R.
2. Set the diagonal element of R to zero.
3. Find the first non-zero element in R. Call this element [e]
4. Find the corresponding row in the matrix which has zeros to the left of column (e) and a 1 in column [e]. Call this row S.
5. If R[i]=1 then subtract S from R. if R[i]=1 then add S to R.
6. Continue with steps 3,4, and 5 until there are no non-zero values left or no row can be found in step 4. In the first case, you have determined an APPROXIMATE test (based on the columns used in the addition or subtraction). In the second case, there is no approximate test available.

If there is neither a DIRECT nor an APPROXIMATE test, next look for a conservative test. There are two types of conservative tests: CONCLUDE SIGNIFICANT ONLY and CONCLUDE INSIGNIFICANT ONLY. A CONCLUDE SIGNIFICANT only test occurs when the denominator contains an extra term and is therefore too big. If the test is significant with a denominator that is too big, then the test with a proper sized denominator would surely have been significant. If the test is insignificant, perhaps the term being tested is insignificant or perhaps the extra term in the denominator is significant. You cannot tell. That is why the test is CONCLUDE SIGNIFICANT ONLY.

A CONCLUDE INSIGNIFICANT ONLY test type has one extra term in the numerator (one too few in the denominator). If the test is insignificant, then both terms in the numerator are insignificant; so in particular the tested term is insignificant. If the test is significant, we cannot tell which term is the cause.

Having computed all possible tests (both test type and term tested by) the next step is to compute the minimal detectable difference. The minimal detectable difference is the magnitude of an effect that can be detected by this experiment design. In particular, we assume an alpha error of 0.05 and a beta error of 0.10 and express the minimal detectable difference as the number of standard deviations of the denominator in the test. For example, a minimal detectable difference of 2.0 means the effect of that term must be twice as big as the denominator in the test in order to be 90% certain the experiment will declare it significant. The minimal detectable difference depends on four quantities: the df for the numerator, the df for the denominator, the coefficient preceding the term in the EMS, and whether the term is fixed or random. In particular, the minimal detectable difference (delta) for a fixed term is given by $$\Delta = \sqrt{2\lambda/C}$$

where lambda is the non-centrality parameter of the non-central F distribution achieving alpha error =0.05 and beta error =0.10, and C the coefficient from the EMS. For a random term delta is given by $$\Delta = \sqrt{(F_{0.5} \times F_{.90} - 1)/C} .$$

where F represents the central F distribution. For significant only tests a heuristic correction is made to the delta value. If the extra term in the denominator is a two factor interaction, then 0.5 is added to delta. If it is a three factor interaction then 0.25 is added. Otherwise the delta is unchanged. To help the user in understanding minimal detectable differences, we categorize the deltas according to the following scheme:

> delta < .5 extremely small
> .5 <= delta < 1.5 small
> 1.5 <= delta <= 3 medium
> 3 <= delta < 5 large
> delta > 5 extremely large Within the expert system the results of this design evaluation are represented in KEE frames. A class unit is set up, called TERMS which contains slots for storing critical information about the terms of the math model. Each term is represented as an individual unit which is a child of the TERMS class. Each child of the TERMS class inherits slots for storing the calculated values. Thus, for each term, there are slots available for storing degrees of freedom, test type, minimal detectable differences, etc.

Communicating the Design (Block 18)

FIG. 4 shows a sample screen which summarizes the design information calculated in block 16.

The system also provides an English summary upon request. For example, the English summary of the design displayed in FIG. 4 would be as follows:

"The following terms have a direct test: main effects, and AB. This is the best type of test. The following terms have medium detectable differences in this design: main effects, and AB. This means that you have moderate information available on these terms."

Redesigning (Block 22)

Once the user has viewed the initial design they may wish to change some of the input characteristics to achieve the appropriate delta while still keeping the experiment cost within budget. The user has the option of changing the design in any one of several ways:

1. The user may change the original input information directly by going back to the Experiment Information form (FIG. 2).
2. The user may ask the system to find a design with the appropriate detectable sizes. If so, the system does a state space search (varying the number of factor levels for each factor) using branch and bound search with a dynamic programming algorithm Artificial Intelligence by P. H. Winston (1984). The system returns the smallest design satisfying the user's criteria for delta.
3. The user may tell the system to assume some terms negligible in its calculation of tests in block 16. Those terms which the user specifies will automatically be set to zero in the EMS matrix thus allowing more tests to be found. These assumptions may later be verified during data analysis.
4. The user may fractionate the design. The process of fractionation will be described hereinafter under the Screening goal.

The expert system suggests potential changes to a design based on a set of forward chaining rules. A copy of the rule set for non-regression experiments is shown in Appendix A.

The expert system stores all designs which are generated during the redesign process. This is accomplished through a "worlds" mechanism (KEE feature) which provides the means of representing context. Every value which is calculated and stored in the expert system is context dependent. The context will change depending on which design the user is working with. As an example Term $AC[ik]$ may have the value 5 for its degrees of freedom slot in Design 1, and have the value 6 for its degrees of freedom slot in Design 2. The unit and slot are the same but the context (design world) is different.

Each design inherits all information from its parent design (the design from which it was created). User changes and values calculated from user changes override this inheritance. This provides an efficient means of storing a large number of design alternatives at once.

Creating a Layout Sheet (Block 22)

Once the user approves a design, a layout sheet may be generated. This layout sheet acts as a blue print for the experiment, describing exactly which combinations of factor levels to run and in what order to run them.

The expert system obtains from the user the level settings for each of the factors and then writes an input program in SAS code to generate the layout sheet. The expert system calls SAS from KEE via UNIX. This is done in the following manner:

1. Create flat Unix file "infile" (SAS program)
2. Call SAS on the program specified in "infile"
3. SAS produces "outfile" as per "infile" instruction.
4. Read "outfile" Shown below is example SAS code for an experiment which two factors A and B. The levels for A are 1,2,3, and 4 and the levels for B are one and two.

```
filename outfile '/ ...;
filename outfile2 '/ ...;
filename prntfile '/ ...;
proc printto print=prntfile log=logfile new;
data _sheet_;
Y = '___';
do _A = 1 to 4;
do _B = 1 to 2;
do _rep _ = 1 to 2;
_random_=ranuni (0);
output;
end;
end;
end;
run;
data _sheet_;set _sheet_;
length
B $ 4;
if _A = 1 then A = 1;
if _A = 2 then A = 2;
if _A = 3 then A = 3;
if _A = 4 then A = 4;
if _B = 1 then B = 'one';
if _B = 2 then B = 'two';
run;
data _sheet_;set _sheet_;
label
A = 'A'
B = 'B'
Y = 'Y'
run;
proc sort;
by _random_;
run;
proc fsprint;
var A B Y;
run;
data _sheet_;set _sheet_;
file outfile;
put _n_ A B Y;
run;
data _sheet_;set _sheet_;
file outfile2;
put _n_ A B _rep_ ;
```

-continued

```
run;
    The input code directs SAS to create the
layout sheet which is shown below.
OBS  A   B      Y
1    4   one   ___
2    3   one   ___
3    1   one   ___
4    2   one   ___
5    3   two   ___
6    3   two   ___
7    1   two   ___
8    2   two   ___
9    4   two   ___
10   4   two   ___
11   2   one   ___
12   1   two   ___
13   1   one   ___
14   2   two   ___
15   3   one   ___
16   4   one   ___
```

In this layout sheet the numbers in the left hand column are observation numbers. The blanks in the far right hand column indicate spaces for the user to record the observations from the experiment.

Analysis of Data (Block 24)

Once the user returns with experimental data, the expert system writes SAS code to do the analysis. As an example, for the experiment with factors A and B, no nesting, the following represents the relevant SAS code for computing Sums of Squares over the data set.

```
1   infile datafile;
2   input __num__ A S B S Y1;
3   run; /* input data from file */
4   proc glm outstat = stat__s;
5   class A B;
6   model Y1 = A B A*B / ss1;
7   output out=pout;
8   run; /* calculate sums of squares */
9   data stat__s; set stat__s; file statfile;
10  put '((" __source__ "' ' __name__ ') ' ss df ')';
11  run; /* output sums of squares and df to a
            file called statfile */
```

The math model representation generated in block 14, easily converts to the SAS model specified in line 6. The sum of squares values output to a file for each term in line 10 are read back in by the expert system after the SAS program finishes running and are stored in slots for each term. From the Sum of Squares and information previously determined in creating the design, the expert system uses standard formulas to compute the mean Squares, F Tests and P Values for each term in the model.

Communicating the Analysis (Block 26)

In FIG. 5 a sample screen is displayed which shows how the user sees the summary of analysis information calculated in block 24.

SCREENING

Inputs (Block 10)

When the goal is Screening the inputs gathered from the user in block 10 include those used in complicated influence. The user is also required to enter information about the interactions between the factors to be studied. This information is input through the KEE form shown in FIG. 6. The user tells the system which terms are of interest and which terms are not to be confounded with terms of interest. Optionally the user may specify a maximum experiment size, factors which are expensive (or inexpensive) to generate combinations for, a maximum term order to study, or any terms to be assumed negligible.

Design Generation (Block 12)

Fractionation is the procedure for finding the smallest experiment which studies the terms of interest without violating any other user restrictions on confounding. There are two modes of doing fractionation in the expert system of the present invention. The first is to minimize the number of runs based on a set of user constraints for terms of interest the second is to find the maximum information given a maximum experiment size.

Mode 1: Minimize Total Experiment Size

The user supplies two sets of terms: interesting (terms of interest) and non-negligible (terms not confounded with terms of interest). The set of interesting terms consists of all terms that the user thinks may be important and wants to estimate. This set includes all main effects plus all user-specified interactions: two factor interactions, three factor interactions, etc. The set of non-negligible terms consists of all other terms that could have an effect on the response variable. The set of interesting terms will not be confounded with themselves nor with any non-negligible term. However, the non-negligible terms can be confounded among themselves.

To find the smallest balanced design, the expert system starts by decomposing each factor into its prime components. For example, if A has six levels, break A into A1 having two levels and A2 having three levels. Next, translate interactions on the original factors into interactions on the prime components. Separately collect all interactions having the same prime components and find the smallest design meeting the requirements. The expert system uses the SAS procedure FACTEX to find the smallest design for each of the individual prime components. The expert system then crosses all of the components. The interactions involving different prime components are automatically estimated by the nature of the crossing.

An example helps illustrate the procedure. Suppose factor A has 2 levels, B has 4 levels, C has 3 levels, and D has 6 levels. Suppose the interesting set consists of the main effects only and the non-negligible set is empty. Break B into B1 and B2 each at 2 levels. Break D into D1 at 2 levels and D2 at 3 levels. The entire interesting set becomes A, B1, B2, B1B2, C, D1, D2, and D1D2. The interesting set for the 2 level primes is (A, B1, B2, B1B2, D1). The interesting set for the 3 level primes is (C, D2).

Input SAS code for the FACTEX procedure for the above experiment is shown below. For a more detailed example of this procedure, see pages 11-14 of the aforementioned Research Publication GMR 7111.

```
FILENAME OUTFILE "/...";
FILENAME NOTESFIL "/...";
PROC FACTEX NOCHECK;
TITLE '2';
FACTORS A __2__1B __2__2B __2__1D /NLEV=2;
SIZE DESIGN = MIN;
MODEL ESTIMATE = (A __2__1B __2__2B __2__1B*__2__2B
   __2__1D);
```

-continued

```
EXAMINE ALIASING (4);
OUTPUT OUT = TMP1
[ A]=A2 NVALS=(1,2)
[ _2_1B _2_2B]=B2 NVALS=(1,2,3,4)
[ _2_1D]=D2 NVALS=(1,2);
RUN;
PROC FACTEX;
TITLE '3';
FACTORS  C _3_1D /NLEV=3;
SIZE DESIGN = MIN;
MODEL ESTIMATE = (C _3_1D);
EXAMINE ALIASING (2);
OUTPUT OUT = TMP2 OUTER_REP=TMP1
[ C]=C3 NVALS=(1,2,3)
[ _3_1D]=D3 NVALS=(1,2,3);
RUN;
DATA; SET TMP2;
A=A2;
B=B2;
C=C3;
D=D3+3*(D2-1);
FILE OUTFILE;
PUT A B C D;
RUN;
PROC MEANS DATA=TMP1 NOPRINT;
TITLE;
OUTPUT OUT=MTMP1 N=N;
RUN;
DATA;SET MTMP1;
FILE NOTESFIL;
PUT N;
RUN;
PROC MEANS DATA=TMP2 NOPRINT;
TITLE;
OUTPUT OUT=MTMP2 N=N;
RUN;
DATA;SET MTMP2;
FILE NOTESFIL MOD;
PUT N;
RUN;
```

Handling expensive combinations is accomplished as follows. Collect all the expensive factors, collect all the inexpensive factors, and perform the above procedure on each set, crossing the results when completed. By working with the expensive factor separately we assure that the number of expensive combinations is minimized. However, since we cross this design with the inexpensive combinations, the total size of the experiment is likely to be larger than a combined design with no expensive factor specified.

Mode 2: Maximize Information Given An Experiment Size Limitation

This is accomplished similarly to Mode 1 but with an iterative procedure added to find the best possible design which meets the users criteria.

Step 1—Decompose each factor into its prime components.

Step 2—Collect all similar prime components, i.e., all two level components, all three level components, all five level components, etc.

Step 3—Find the minimal size for each prime component using the SAS procedure FACTEX. Estimate all main effects. If no design is found then stop.

Step 4—If the product of the minimal sizes is less than the maximum allowed, repeat step 3 but estimate main effects and include 2 factor interactions as non-negligible.

Step 5—If the product of the minimal sizes is less than the maximum allowed, repeat step 3 but estimate main effects and 2 factor interactions.

Step 6—Continue incrementally increasing the order of terms to be estimated (or considered non-negligible) until the experiment size limitation is violated or a full factorial design is generated. In the latter case return the full factorial design, in the former case return the largest design which was generated that did not violate the size limitation.

In both Mode 1 and Mode 2 a confounding pattern must be discovered which corresponds to the design. For basic cases, where all factors have the same prime number of levels, the confounding pattern is simply returned by the FACTEX procedure. However, added computation must be performed whenever any kind of crossing of designs or any kind of prime level factorization occurs. Crossing occurs whenever there are mixed primes, whenever there are non-prime level factors, whenever there is nesting, and whenever there are expensive combinations.

To find the confounding in factors that are not primes, simply replace any occurrence of the prime component with the original factor. For example, if A has 4 levels, with prime components A1 and A2, then all of the following interactions equal AB: A1B, A2B, A1A2B. Any occurrences of these prime components should be replaced with the interaction involving the original factors.

Whenever two components are crossed, the confounding generated by the crossing must be determined. The following description illustrates crossing two components. This should illustrate the procedure for any number of components. Start with the confounding pattern for component 1. Additional confoundings are generated by multiplying each term in component 1 by the identity pattern in component 2. Next, multiply each term in component 2 by the identity pattern in component 1. Complete this pattern by multiplying each line in component 1 by each line in component 2. By convention we will assign the whole confounding string to the lowest order term, breaking ties alphabetically. Common terms are combined. For a more detailed example of this procedure, see pages 13-14 of the aforementioned Research Publication GMR 7111.

Constructing a Mathematical Model (Block 14)

The procedure for generating a mathematical model for fractional designs is the same as that for full factorial designs under Complicated Influence. The only differences that is allowed is that the user may specify a maximum order beyond which the system will stop generating terms. So for instance, if the user specifies a maximum order of 3, the system would not generate the ABCD interaction.

Design Evaluation (Block 16)

The evaluation of fractionated designs is similar to that of Complicated Influence. The differences are described below.

Computation of degree of freedom is based on the eventual analysis of data using the type I(one) computational method for analysis, sorted by order and alphabetically within an order. This is handled using the prime factorization technique discussed in connection with block 12. For each confounding string, define the primary term as the term with the lowest order, breaking ties alphabetically. Then the df for that string gets assigned to the primary term. The df for each confounding string in a p-level fractional design is p-1. When a p1-level design is crossed with a p2-level design, the cross product terms each have (p1-1)(p2-1) df.

A slight alteration of the full factorial EMS algorithm handles the fractionation case. Start by computing the EMS for every term using the full factorial algorithm (Lorenzen 1977). Next alter every coefficient by multiplying by the fraction in the experiment (e.g. ½, ⅓, 1/6). Any coefficient less than one gets replaced by one. Finally, calculate the EMS for every primary term by forming the union of all confounded terms.

The search for tests is the same as describe in block 16 of Complicated Influence except that we look for a test on the primary term before looking for a test on the confounding string.

The number of runs in Screening is calculated simply by counting the number of lines in the design generated by FACTEX in block 12.

Communicating the Design (Block 18)

This step is the same as for Complicated Influence.

Redesigning (Block 20)

Once the user has viewed the initial design he/she may wish to change some of the input characteristics to achieve the appropriate delta while still keeping the experiment cost within budget. The user has the option of changing the design in any one of several ways:

1. The user may change the original input information directly by going back to the Experiment Information form of FIG. 2.
2. The user may tell the system to assume some terms negligible in its calculation of tests in block 16. Those terms which the user specifies will automatically be set to zero in the EMS matrix thus allowing more tests to be found. These assumptions may later be verified during data analysis.
3. The user may re-fractionate the design, changing the terms of interest or terms not to be confounded with terms of interest.
4. The user may tell the system to generate a full factorial design.

The expert system stores all designs which are generated during the redesign process as described in Complicated Influence. The expert system will suggest potential redesign options using the rule set listed in Appendix A.

Creating a Layout Sheet (Block 22)

Once the user approves a design, a layout sheet is generated. This layout sheet acts as a blue print for the experiment, describing exactly which combinations of factor levels to run and in what order to run them. In fractional designs the layout sheet is generated based on the design created by FACTEX. An example of the SAS code for doing this is as follows:

```
filename datafile '/ . . . ;
filename outfile '/ . . . .;
filename outfile2 '/ . . . ;
filename prntfile '/ . . . ;
proc printto print=prntfile log=logfile new;
data _sheet_;
Y = '__';
infile datafile;
input _A _B _C _D ;
run;
data _sheet_;set _sheet_;
_random_ = ranuni(0);
_count_ = _n_ - 1;
_rep_ = mod(_count_,1) + 1;
run;
data _sheet_;set _sheet_;
```

-continued

```
length;
if _A = 1 then A = 1;
if _A = 2 then A = 2;
if _B = 1 then B = 1;
if _B = 2 then B = 2;
if _B = 3 then B = 3;
if _B = 4 then B = 4;
if _C = 1 then C = 1;
if _C = 2 then C = 2;
if _C = 3 then C = 3;
if _D = 1 then D = 1;
if _D = 2 then D = 2;
if _D = 3 then D = 3;
if _D = 4 then D = 4;
if _D = 5 then D = 5;
if _D = 6 then D = 6;
run;
data _sheet_;set _sheet_;
label
A = 'A'
B = 'B'
C = 'C'
D = 'D'
Y = 'Y';
run;
proc sort;
by _random_;
run;
proc fsprint;
var A B C D Y;
run;
data _sheet_;set _sheet_;
file outfile;
put _n_ A B C D Y;
run;
data _sheet_;set _sheet_;
file outfile2;
put _n_ A B C D _rep_ ;
run;
```

Analysis of Data (Block 24)

Formal analysis of variance is performed for each response variable. To analyze the data the proper model is generated for SAS. The terms must be in a specific order: the lowest order terms appearing first, and within each order the terms must appear in the order that the factors were entered into the system. Only the primary term in each confounding list is used. Given this model, PROC GLM in SAS is used to compute the Type 1 Sum of Squares and from this to compute means squares, F-tests and P-values. (see discussion under Complicated Influence)

Communicating the Analysis (block 26)

The analysis is communicated as in complicated influence.

ROBUST DESIGN

Inputting to the Computer (Block 10)

See the discussion's under Complicated Influence and Screening. In addition the following information is stored for each factor.

Control/Noise—The user indicates whether the factor is a control factor or a noise factor. The purpose of a robust design is to find the values of the control factors which minimize the effect of the noise factors.

Fractionation (Block 12)

This feature is available for Robust Designs and operates the same as described in Screening.

Constructing a Mathematical model (Block 14)

Two math models are constructed for Robust Experiments. An All factors math model and a Control factors only math model.

The procedure for generating a mathematical model for All Factors in robust designs is the same as that for full factorial designs in Complicated Influence or fractional designs in Screening depending on whether or not the user fractionates.

For Control Factors a second Mathematical Model is derived using only the control factors to generate the terms in the model.

Design Evaluation (Block 16)

For All Factors the evaluation of robust designs is similar to that of Screening or Complicated Influence.

For Control Factors design evaluation is done using the same procedure described for All Factors with the exception that the coefficient for each term is computed using the following algorithm.

1. Compute the number of different control factor combinations which exist in the design.
2. Compute the fraction of the noise combinations that are run for each control combination.
3. Multiply each coefficient in the model by the fraction of noise combinations considered.

The Control Factors design information is stored in a separate world within the worlds mechanism (described in Complicated Influence). This world inherits from the All Factors design world any information which is not calculated.

Communicating the Design (Block 18)

Both design models are communicated to the user in the same form as Complicated Influence and Screening experiments.

Redesigning (Block 20)

Redesign is accomplished in the same way as in Screening and Complicated Influence. Redesign worlds are always created as children of the All Factors design world.

Creating a Layout Sheet (Block 22)

Creating a layout sheet is the same as in Screening and Complicated Influence.

Analysis of Data (Block 24)

Formal analysis of variance is performed for each response variable in the same way for the All Factors design as in Complicated Influence or Screening.

For the Control Factors design three types of analysis are offered:

1. means calculated over the noise factors
2. log of the standard deviation calculated over the noise factors
3. quadratic loss function, combining closeness to target and variability caused by the noise factors.

Using SAS, a data set is created which contains the means, variance, and standard deviation of the response variable calculated over the noise factors. This data set is then analyzed according to the users selection of the type of analysis required. Example SAS code for a three factor experiment (A and B control, and a noise factor) where the user wished to analyze the log of the quadratic loss function is shown below:

```
1   infile datafile;
2   input _n_ A B mY1 vY1 sY1 ;
3   _M = mY1;
4   _V = vY1;
5   _S = sY1;
6   _Y = log(1*(_M**2+_V));  /* loss function with target = 0
                                 and k = 1 */
7   run;
8   proc glm outstat=stat_s;
9   class A B;
10  model _Y = A B A*B / ss1;
11  output out=pout p=pY r=rY;
12  run;
13  data stat_s; set stat_s;file statfile;
14  put '((" _source_ "' ' _name_ ') ' ss df ')';
15  run;
```

The equation in line 6 will vary according to the type of Control Factors analysis the user requests. Line 14 outputs Type 1 Sums of Squares and from this, mean squares, F-tests and P-values are calculated (see Complicated Influence)

Communicating the Analysis (Block 26)

The analysis is communicated as in Screening or Complicated Influence for both the All FACTORS analysis and the Control Factors analysis.

MODEL RESPONSE

Inputting to the Computer (Block 10)

Inputs are gathered from the user through a series of interactive forms which are shown in FIG. 7. The factor information is stored in the KEE frames structure, with each factor represented as an individual unit which is a child of the FACTORS class. Each child of the FACTORS class inherits slots for storing the user's input. The following slots store the critical information for each of the user's factors in complicated influence:

1. Abbreviation—a short string used to represent the factors effect in the math model representation.
2. Lower Bound—The lower bound on the factor range in a production setting.
3. Upper Bound—The upper bound on the factor range in a production setting.
4. Type—Must be fixed.
5. Quantitative-or-Qualitative—A factor is quantitative if it has meaningful numbers associated with its levels. Otherwise it is qualitative.

In addition to information on individual factors the user also enters the type of Model (one of Plackett-Burman, Central Composite, Box-Behnkan, or D-Optimal), and any run order restrictions (i.e. an inability of disinclination to change the levels of a factor frequently from one experiment trial to the next).

Generating a Design (Block 12)

The design which is generated depends on the inputs provided by the user. Plackett-Burman designs are generated using SAS. An example input SAS file generated by the expert system for a 4 factor Plackett-Burman experiment is as follows:

```
%INCLUDE "!sasroot/sasmacro/adxgen.sas";
%INCLUDE "!sasroot/sasmacro/adxff.sas";
%adxinit
```

```
%adxpbd(out,4)
FILENAME OUTFILE "/users/doe/users/scott/sasfiles/fract.des";
DATA OUT;SET OUT;
FILE OUTFILE;
PUT _N_ T1-T4;
RUN;
PROC PRINT DATA=OUT; RUN;
```
Box-Behnkan designs are stored in tables in Unix files. These can be referenced by the number of factors in the design. The tables are stored assuming upper bounds of 1 and lower bounds of negative 1 and then scaled by the users inputs.

Central Composite designs are generated using SAS. An example input SAS file generated by the expert system for a 3 factor Central Composite experiments is as follows:

```
%INCLUDE "!sasroot/sasmacro/adxgen.sas";
%INCLUDE "!sasroot/sasmacro/adxcc.sas";
%INCLUDE "!sasroot/sasmacro/adxff.sas";
%adxinit
%adxccd(out,3,8,9,1.668)
FILENAME OUTFILE "/users/doe/users/scott/sasfiles/fract.des";
DATA OUT;SET OUT;
FILE OUTFILE;
PUT _N_ T1-T3;
RUN;
PROC PRINT DATA=OUT; RUN;
```

D-optimal designs are generated using SAS. An example input SAS file generated by the expert system for a 3 factor D-optimal experiment with A linear and qualitiative (three levels), B quadratic quantitative and C quantitative cubic is as follows:

In the D-Optimal case, the user specifies the polynomial model to be fit.

Restrictions on randomization are added as terms in the model in the same manner as for Complicated Influence experiments.

```
data cand;
do A=1.0,5.0;
do B=1.0,3.0,5.0;
do C=1.0,2.333,3.667,5.0;
output;
end;
end;
end;
run;
data cand; set cand;
A=0.5*A-1.5;
B=0.5*B-1.5;
C=0.5*C-1.5;
run;
proc optex data=cand nocode;
model  A B B*B C C*C C*C*C A*B A*C B*C ;
examine design;
generate n=20;
output out=out;
run;
FILENAME OUTFILE "/users/doe/users/scott/sasfiles/fract.des";
DATA OUT;SET OUT;
FILE OUTFILE;
PUT _N_ A B C;
RUN;
PROC PRINT DATA=OUT;
RUN;
```

Constructing a Mathematical Model (Block 14)

For model response experiments the mathematical model is simply the polynomial equation that will be fit using regression techniques. This model is determined by the type of design the user asks for. The types of designs offered by the expert system along with their associated model are listed below:
1. Plackett-Burman—Linear model
2. Box-Behnkan—Quadratic Model
3. Central Composite—Quadratic Model
4. D-Optimal—General All effects in the experiment which are not fixed at a given level and not related to the input factors are represented by the error term which is nested in every other factor.

Design Evaluation (Block 16)

The mathematical model and the design are the basis for evaluating the properties of the design. These properties include:
1. Degrees of Freedom for each Term (df)
2. The type of test available on each Term
3. The terms testing each Term
4. The test degrees of freedom for each Term 5. The detectability of each term (delta)
6. A classification for the detectability for each term
7. The Expected Mean Squares for each term (EMS)
8. The required experiment size (number of runs)

Each quantitative term in the model has one df. The df for qualitative factors are one less than the number of levels.

All terms are tested by error and have DIRECT tests unless there is a restriction on randomization. In this case, the tests are of the type CONCLUDE INSIGNIFICANT ONLY.

EMS is calculated using the algorithm described in Sample Size Choice, by Odeh and Fox, Published in 1975 by Marcell Decker, page 31ff.

The calculation of the minimal detectable difference uses the same algorithm described in Complicated Influence by determining the appropriate coefficient C. This is done using the following procedure:

1) Rescale the problem so that the lowest value corresponds to 1 and the highest value to $-1$.
2) For scaled X levels of the term, $$C = \Sigma X^2/2 \quad (X \text{ quantitative}),$$

3) For qualitative term, $$C = \frac{I}{\sum_{i=1}^{I} (1/n_i)} \quad (X \text{ qualitative}),$$

where I is the number of levels of the term in the design and n(i) is the number of times the ith level of X occurs in the design.

4) If the term is the product of a quantitative term Y and a qualitative term Z, $$C = \frac{I}{\sum_{i=1}^{I} (1/\Sigma Y_i^2/2)} \quad (Y \text{ quantitative}, Z \text{ qualitative}),$$

where I is the number of levels of Z in the design and $Y_i$ is summed over the $i^{th}$ level of Z.

The detectable difference classification is accomplished as described in Complicated Influence. The number of runs in the design is simply the size of the design generated in block 12.

Communicating the Design (Block 18)

The design is communicated as in Complicated Influence.

Redesigning (Block 20)

Once the user has viewed the initial design he/she may wish to change some of the input characteristics to achieve the appropriate delta while still keeping the experiment cost within budget. The user has the option of changing the design in any one of several ways:

1. The user may change the original input information directly by going back to the Experiment Information form (FIG. 7).
2. In some model types the user may change the number of Center Repeats.
3. The user may change some properties of the design, such as Rotatability or Orthoganality or the alpha value for Central Composite.
4. In D-Optimal Designs, the user may exclude points from the candidate space or enter specific points to run in the design.

Suggestions for Redesign are given based on the rule base listed in Appendix B. Designs are stored in the same manner as described in Complicated Influence.

Creating a Layout Sheet (Block 22)

A layout sheet is generated as described in Screening.

Analysis of Data (Block 24)

Once the user returns with experimental data, the expert system writes SAS code to do the analysis. As an example, for the experiment with factors A, B and C all quantitative and quadratic the following SAS code would be generated.

```
1   infile datafile;
2   input _num_ A B C Y1;
3   run;  /* input data from file */
4   data _sheet_; set _sheet_;
5   C1 = A;
6   C2 = A*A;
7   C3 = B;
8   C4 = B*B;   /* define parameters */
9   C5 = A*B;
10  C6 = C;
11  C7 = C*C;
12  C8 = A*C;
13  C9 = B*C;
14  proc reg covout outest=eststats singular=1E-15
15  model Y1 = C1 C2 C3 C4 C5 C6 C7 C8 C9 ;
16  data eststats; set eststats; file estfile;
17  put _depvar_ _type_ intercep C1 C2 C3 C4 C5 C6 C7 C8 C9 ;
18  run;  /* output parameter estimates and standard error
                                                  to file */
```

The math model representation created in block 14 is used to create parameters C1–C9 in steps 4 through 13 above. The parameter estimates and standard error which are output to a file for each term in line 18 are read in by the expert system after the SAS program finishes running.

Using the standard error, test degrees of freedom, and the parameter estimates, the expert system calculates T values and P values using standard formulas.

Communicating the Analysis (Block 26)

In FIG. 8 a sample screen is displayed which shows how the user sees the summary of analysis information calculated in block 24.

Appendix A.
```
((add.assumptions.to.get.tests
   (if (the tests
           of
           current.design
           is
           some.not.tested)
       (the fractionated of current.design is yes)
       (lisp (null (default-assumptions-useful))))
       then
       (the suggestion
           of
           current.design
           is
           (assumptions because
                   some.terms.not.tested))
       (the assumption.level
           of
           current.design
           is
           (lisp (get-resolution-size)))))
 (add.default.assumptions.to.get.tests
   (if (the tests of current.design is
                       some.not.tested)
       (the fractionated of current.design is yes)
       (lisp (default-assumptions-useful)))
       then
       (the suggestion
           of
           current.design
           is
           (default-assumptions because
                   some.terms.not.tested))))
 (add.repeats.to.get.tests
   (if (the tests
           of
           current.design
           is
```

```
                 highest.order.not.tested)
        (the repetitions of current.design is 1)
        (the fractionated of current.design is no)
        then
        (the suggestion
             of
             current.design
             is
             (increase.reps because
                       highest.order.not.tested))))
(bad.deltas.not.fractionated
   (if (cant.find (the deltas of current.design is ok))
       (cant.find (the fractionated of
                              current.design is yes))
       then
       (the suggestion
             of
             current.design
             is
             (change.term.info because user.said.bad.deltas))))
(deltas.too.big.assumptions
   (if (the deltas of current.design is too.big)
       then
       (the suggestion
             of
             current.design
             is
             (assumptions because
                       user.said.deltas.too.big))
       (the assumption.level
             of
             current.design
             is
             (lisp (get-resolution-size)))))
(deltas.too.big.fractionated
   (if (the deltas of current.design is too.big)
       (the fractionated of current.design is yes)
       then
```

```
        (the suggestion
            of
            current.design
            is
            (refractionate.more.terms because
                            user.said.deltas.too.big))
        (the suggestion
            of
            current.design
            is
            (assumptions because user.said.deltas.too.big))
        (the assumption.level
            of
            current.design
            is
            (lisp (get-resolution-size)))
        (the suggestion
            of
            current.design
            is
            (increase.reps because user.said.deltas.too.big))))
(deltas.too.small.fractionated1
    (if (the deltas of current.design is too.small)
        (the fractionated of current.design is yes)
        (the repetitions of current.design is 2)
        then
        (the suggestion
            of
            current.design
            is
            (decrease.reps because
                            user.said.deltas.too.small))))
(deltas.too.small.fractionated2
    (if (the deltas of current.design is too.small)
        (the fractionated of current.design is yes)
        (the repetitions of current.design is 1)
        then
        (the suggestion
```

```
                of
                current.design
                is
                (refractionate.less.terms because
                                user.said.deltas.too.small))))
(experiment.too.big.factorial.fixed
  (if (the size of current.design is too.big)
      (the fractionated of current.design is no)
      (the ask.for.fractionated of current.design is no)
      (the factor of current.design is ?f)
      (lisp (eql (get-current-world-value ?f 'fixed.or.random)
            'fixed))
      (lisp
        (eql (get-current-world-value ?f
                                'quantitative.or.qualitative)
            'quantitative))
      (lisp (> (get-current-world-value ?f 'number.of.levels)
            3))
      then
      (the suggestion
           of
           current.design
           is
           (reduce.levels of ?f because experiment.too.big))))
(experiment.too.big.factorial.random
  (if (the size of current.design is too.big)
      (the fractionated of current.design is no)
      (the ask.for.fractionated of current.design is no)
      (the factor of current.design is ?f)
      (lisp (eql (get-current-world-value ?f 'fixed.or.random)
            'random))
      (lisp (> (get-current-world-value ?f 'number.of.levels)
            2))
      then
      (the suggestion
           of
           current.design
           is
```

```
              (reduce.levels of ?f because experiment.too.big))))
(experiment.too.big.factorial2
   (if (the size of current.design is too.big)
       (the fractionated of current.design is no)
       (the ask.for.fractionated of current.design is no)
       (the all.two.levels of current.design is yes)
       (the repetitions of current.design is 1)
       then
       (the suggestion
           of
           current.design
           is
           ("FRACTIONATE" because experiment.too.big))))
(experiment.too.big.fractionated1
   (if (the size of current.design is too.big)
       (the ask.for.fractionated of current.design is yes)
       (the mixed.unmixed of current.design is mixed)
       then
       (the suggestion
           of
           current.design
           is
           (unmix because experiment.too.big))))
(experiment.too.big.fractionated2
   (if (the size of current.design is too.big)
       (the ask.for.fractionated of current.design is yes)
       (the mixed.unmixed of current.design is unmixed)
       then
       (the suggestion
           of
           current.design
           is
           (refractionate.less.terms because
                              experiment.too.big))))
(experiment.too.big.fractionated3
   (if (the size of current.design is too.big)
       (the ask.for.fractionated of current.design is yes)
       (the all.two.levels of current.design is no)
```

```
       then
       (the suggestion
           of
           current.design
           is
           (reduce.levels because experiment.too.big))))
(experiment.too.big.fractionated4
   (if (the size of current.design is too.big)
       (the ask.for.fractionated of current.design is yes)
       (the all.two.levels of current.design is no)
       (the factor of current.design is ?f)
       (lisp
          (eql (get-current-world-value ?f
                                   'quantitative.or.qualitative)
               'qualitative))
       (lisp
          (member (get-current-world-value ?f
                                       'number.of.levels)
             '(5 7 11 13 17 19 23)))
       then
       (the suggestion
           of
           current.design
           is
           (bump.levels of ?f because experiment.too.big))))
(experiment.too.big.reps
   (if (the size of current.design is too.big)
       (the repetitions of current.design is 2)
       then
       (the suggestion
           of
           current.design
           is
           (decrease.reps because experiment.too.big))))
(experiment.too.big.taguchi
   (if (the size of current.design is too.big)
       (the goal of current.design is taguchi)
       (the ask.for.fractionated of current.design is yes)
```

```
            then
            (the suggestion
                of
                current.design
                is
                (remove.control.noise.interactions because
                                            experiment.too.big))))
    (no.tests
      (if (the tests of current.design is none)
          (lisp
            (or (get-current-world-value (get-experiment-unit)
                                            'assumptions)
                (null
                  (get-current-world-value (get-experiment-unit)
                                            'default.assumptions))))
          then
          (the suggestion
                of
                current.design
                is
                (assumptions because no.tests))
          (the assumption.level
                of
                current.design
                is
                (lisp (get-resolution-size)))))
    (no.tests.default.assumptions
      (if (the tests of current.design is none)
          (lisp
            (and
              (null
                (get-current-world-value (get-experiment-unit)
                                            'assumptions))
              (get-current-world-value (get-experiment-unit)
                                            'default.assumptions)))
          then
          (the suggestion
                of
```

```
                  current.design
                  is
                  (default-assumptions because no.tests))))
(not.direct.tests.assumptions
   (if (the tests of current.design is not.direct.tests)
       (the poorly.tested.term of current.design is ?t)
       then
       (the assumption
              of
              current.design
              is
              (lisp (get-terms-assumed-to-be-negligible ?t)))))
(not.direct.tests.factorial
   (if (the fractionated of current.design is no)
       (the repetitions of current.design is 1)
       (the tests of current.design is not.direct.tests)
       then
       (the suggestion
              of
              current.design
              is
              (increase.reps because not.direct.tests))))

(random.run.order.impractical
          (if (the run.order of current.design is impractical)
              then
              (the suggestion
                     of
                     current.design
                     is
                     (add.restrictions because run.order.bad))))
       (remove.expensive.blocks
          (if (the size of current.design is too.big)
              (the expensive.vs.inexpensive
                     of
                     current.design
                     is
                     yes)
                  then
```

```
                (the suggestion
                        of
                        current.design
                        is
                        (remove.expensive.blocks because
                                        experiment.too.big))))
        (remove.restrictions.to.get.tests
          (if (the tests of current.design is some.not.tested)
              (the restrictions of current.design is present)
              then
              (the suggestion
                        of
                        current.design
                        is
                        (remove.restrictions because
                                        some.tests.missing))))
(some.term.not.tested.fractionated
   (if (the fractionated of current.design is yes)
       (the tests of current.design is some.not.tested)
       then
       (the suggestion
                of
                current.design
                is
                (refractionate.more.terms because
                                some.tests.missing))))
(test.addition.assumptions
   (if (the tests of current.design is not.direct.tests)
       (the tested.by.addition.term
                of
                current.design
                is
                ?t)
       then
       (the assumption
                of
                current.design
                is
```

```
                (lisp (get-terms-assumed-to-be-
                                  negligible-addition ?t))))))
```

Appendix B:

```
((bad.deltas.central.composite1
    (if (or (the deltas of current.design is too.big)
            (the deltas of current.design is too.small))
        (the model.type
            of
            current.design
            is
            central-composite)
        (the rotatable.and.orthogonal
            of
            current.design
            is
            yes)
        then
        (the suggestion
            of
            current.design
            is
            (change.properties because bad.deltas))))
  (bad.deltas.general
    (if (or (the deltas of current.design is too.big)
            (the deltas of current.design is too.small))
        (or (the model.type of current.design is linear)
            (the model.type of current.design is box-behnken))
        then
        (the suggestion
            of
            current.design
            is
            (change.model.type because bad.deltas))))
  (experiment.too.big.box.behnken
    (if (the size of current.design is too.big)
        (the model.type of current.design is box-behnken)
        then
        (the suggestion
```

```
                of
                current.design
                is
                (change.model.type because experiment.too.big))))
(experiment.too.big.central.composite1
   (if (the size of current.design is too.big)
       (the model.type of current.design is central-composite)
       (the rotatable.and.orthogonal of current.design is yes)
       then
       (the suggestion
                of
                current.design
                is
                (change.properties because experiment.too.big))))
(experiment.too.big.central.composite2
   (if (the size of current.design is too.big)
       (the model.type of current.design is central-composite)
       (the rotatable.and.orthogonal of current.design is no)
       then
       (the suggestion
                of
                current.design
                is
                (decrease.center.reps because experiment.too.big))))
(experiment.too.big.d.optimal
   (if (the size of current.design is too.big)
       (the model.type of current.design is d-optimal)
       then
       (the suggestion
                of
                current.design
                is
                (decrease.experiment.size because
                                        experiment.too.big))))
(impossible.condition1
   (if (the impossible.condition.exists
                of
                current.design
```

```
                is
                yes)
        (cant.find (the model.type of current.design is
                                d-optimal))
        then
        (the suggestion
                of
                current.design
                is
                (change.to.d.optimal because
                                impossible.condition))))
(impossible.condition2
    (if (the impossible.condition.exists of current.design is yes)
        (the model.type of current.design is d-optimal)
        then
        (the suggestion
                of
                current.design
                is
                (enter.impossible.conditions because
                                impossible.condition))))
(larger.deltas.box-behnken
    (if (or (the deltas of current.design is too.small)
            (the deltas of current.design is too.big))
        (the model.type of current.design is box-behnken)
        then
        (the suggestion
                of
                current.design
                is
                (change.model.type because bad.deltas))))
(larger.deltas.central.composite
    (if (the deltas of current.design is too.small)
        (the model.type of current.design is central-composite)
        (the rotatable.and.orthogonal of current.design is no)
        then
        (the suggestion
                of
```

```
            current.design
            is
            (decrease.center.reps because
                                 user.said.deltas.too.small))
      (the suggestion
            of
            current.design
            is
            (decrease.alpha.values
                       because user.said.deltas.too.small))))
(larger.deltas.d.optimal
   (if (the deltas of current.design is too.small)
       (the model.type of current.design is d-optimal)
       then
       (the suggestion
            of
            current.design
            is
            (decrease.experiment.size
                       because user.said.deltas.too.small))))
(restrictions.cause.bad.tests
   (if (the run.order of current.design is ok)
       (the restrictions of current.design is present)
       (the tests of current.design is not.direct.tests)
       then
       (the suggestion
            of
            current.design
            is
            (remove.restrictions because not.direct.tests))))
(run.order.bad
   (if (the run.order of current.design is impractical)
       (cant.find (the restrictions of current.design
                                  is present))
       then
       (the suggestion
            of
            current.design
```

```
                    is
                    (add.restrictions because run.order.bad))))
(smaller.deltas.central.composite
   (if (the deltas of current.design is too.big)
       (the model.type of current.design is central-composite)
       (the rotatable.and.orthogonal of current.design is no)
       then
       (the suggestion
            of
            current.design
            is
            (increase.center.reps because
                              user.said.deltas.too.big))
       (the suggestion
            of
            current.design
            is
            (increase.alpha.values because
                              user.said.deltas.too.big))))
(smaller.deltas.d.optimal
   (if (the deltas of current.design is too.big)
       (the model.type of current.design is d-optimal)
       then
       (the suggestion
            of
            current.design
            is
            (increase.experiment.size because
                              user.said.deltas.too.big)))))
```

We claim:

1. A computer implemented method of designing a robust experiment to be carried out by a user, the method comprising the steps of:
   a. inputting information to the computer, the information including:
      i. a response variable,
      ii. factors to be varied in the experiment,
      iii. factor properties including indications representing which of the factors are noise factors and which of the factors are control factors;
   b. generating an experiment design in accordance with the information input to the computer in step a.;
   c. constructing two mathematical models, the first mathematical model containing terms representing hypothetical effects of all of the factors and the factor interactions on the response variable, the second mathematical model containing terms representing hypothetical effects of the control factors and control factor interactions on the response variable;
   d. evaluating the experiment design generated in step b. by utilizing the information input in step a. and the two mathematical models constructed in step c. to compute values of statistical properties for terms in each of the two mathematical models;
   e. communicating the values computed in step d. to the user;
   f. generating a redesigned experiment by performing steps b. through e. using user changes to the information originally input in step a., until the user is satisfied with the values communicated in step e.;

g. creating a layout sheet specifying individual trials of the redesigned experiment to be performed by the user;

h. performing an analysis of experimental data obtained by the user performing the trials of the redesigned experiment specified by the layout sheet created in step g.; and i. communicating a summary of the analysis performed in step h. to the user.

2. A computer implemented method of designing an experiment to be carried out by a user for studying model response, the steps of the method comprising:

a. inputting information to the computer, the information including:
  i. a response variable,
  ii. a model type to be generated,
  iii. factors to be varied in the experiment, and
  iv. factor properties;

b. generating an experiment design in accordance with the model type input in step a.;

c. constructing a mathematical model containing terms representing hypothetical effects of the factors and interactions between the factors on the response variable;

d. evaluating the experiment design generated in step b. by utilizing the information input in step a. and the mathematical model constructed in step c. to compute values of statistical properties for terms in the mathematical mode;

e. communicating the values computed instep d. to the user;

f. generating a redesigned experiment by performing steps b. through e. using user changes to the information originally input in step a. until the user is satisfied wit the values communicated in step e., wherein the user changes are suggested by a set of expert system forward chaining rules;

g. creating a layout sheet specifying individual trials of the redesigned experiment to be performed by the user;

h. performing an analysis of experimental data obtained by the user performing the trials of the redesigned experiment specified by the layout sheet created in step g.; and i. communicating a summary of the analysis performed in step h. to the user.

3. A computer implemented method of designing a robust experiment to be carried out by a user, the method comprising the steps of:

a. inputting information to the computer, the information including:
  i. a response variable,
  ii. factors to be varied in the experiment, and
  iii. factor properties including indications representing which of the factors are noise factors and which of the factors are control factors;

b. generating an experiment design in accordance with the information input to the computer in step a.;

c. constructing two mathematical models, the first mathematical model containing terms representing hypothetical effects of all of the factors and the interactions between the factors on the response variable, the second mathematical model containing terms representing hypothetical effects of the control factors and interactions between control factors on the response variable;

d. evaluating the experiment design generated in step b. by utilizing the information input in step a. and the two mathematical models constructed in step c. to compute values of statistical properties for terms in each of the two mathematical models;

e. communicating the values computed in step d. to the user;

f. generating a redesigned experiment by performing steps b. through e. using user changes to the information originally input in step a., until the user is satisfied with the values communicated in step e., wherein the user changes are suggested by a set of expert system forward chaining rules;

g. creating a layout sheet specifying individual trials of the redesigned experiment to be performed by the user;

h. performing an analysis of experimental data obtained by the user performing the trials of the redesigned experiment specified by the layout sheet created in step g.; and i. communicating a summary of the analysis performed in step h. to the user, 4. A computer implemented method of designing an experiment to be carried out by a user for studying complicated influence, the steps of the method comprising:

a. inputting information to the computer, the information including:
  i. a response variable,
  ii. factors to be varied in the experiment,
  iii. factor properties including an indication of a number of factor levels for each of the factors, and
  iv. a number of times the experiment is to be repeated;

b. generating a full factorial experiment design in accordance with the information input to the computer in step a.;

c. constructing a mathematical model containing terms representing hypothetical effects of the factors and interactions between all of the factors on the response variable;

d. evaluating the experiment design generated in step b. by utilizing the information input in step a. and the mathematical model constructed in step c. to compute values of statistical properties for terms in the mathematical model, including a minimum detectable difference value for each term in the mathematical model;

e. communication the values computed in step d. to the user;

f. generating a redesigned experiment of minimum size by repeating steps b. through e., while varying the number of factor levels of each of the factors originally input in step a. in accordance with a branch and bound search algorithm, until the minimum detectable difference values computed in step d. are less than user specified values;

g. creating a layout sheet specifying individual trials of the redesigned experiment to be performed by the user;

h. performing an analysis of experimental data obtained by the user performing the trials of the redesigned experiment specified by the layout sheet created in step g.; and i. communicating a summary of the analysis performed in step h. to the user.

* * * * *